(12) United States Patent
Bae et al.

(10) Patent No.: US 10,925,747 B2
(45) Date of Patent: Feb. 23, 2021

(54) INTERVERTEBRAL CAGE

(71) Applicant: IMDS LLC, Providence, UT (US)

(72) Inventors: Hyun Bae, Santa Monica, CA (US); Jeffery D. Arnett, Gilbert, AZ (US); Nicholas Slater, Chandler, AZ (US)

(73) Assignee: IMDS LLC, Providence, UT (US)

( * ) Notice: Subject to any disclaimer, the term of this patent is extended or adjusted under 35 U.S.C. 154(b) by 43 days.

(21) Appl. No.: 15/786,387

(22) Filed: Oct. 17, 2017

(65) Prior Publication Data

US 2018/0104066 A1   Apr. 19, 2018

Related U.S. Application Data

(60) Provisional application No. 62/410,156, filed on Oct. 19, 2016.

(51) Int. Cl.
| | |
|---|---|
| *A61F 2/44* | (2006.01) |
| *A61F 2/46* | (2006.01) |
| *A61F 2/30* | (2006.01) |
| *A61B 17/70* | (2006.01) |

(52) U.S. Cl.
CPC ............ *A61F 2/442* (2013.01); *A61F 2/4455* (2013.01); *A61F 2/4611* (2013.01); *A61B 17/70* (2013.01); *A61F 2/4603* (2013.01); *A61F 2002/3011* (2013.01); *A61F 2002/3092* (2013.01); *A61F 2002/3093* (2013.01); *A61F 2002/30266* (2013.01); *A61F 2002/30281* (2013.01); *A61F 2002/30329* (2013.01); *A61F 2002/30471* (2013.01); *A61F 2002/30515* (2013.01); *A61F 2002/30537* (2013.01); *A61F 2002/30538* (2013.01); *A61F 2002/30578* (2013.01); *A61F 2002/30593* (2013.01); *A61F 2002/30604* (2013.01); *A61F 2002/30616* (2013.01); *A61F 2002/30962* (2013.01); *A61F 2002/4627* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,045,579 A | * | 4/2000 | Hochshuler | A61F 2/4455 606/247 |
| 6,190,414 B1 | * | 2/2001 | Young | A61F 2/447 606/247 |
| 6,443,989 B1 | * | 9/2002 | Jackson | A61F 2/4455 606/247 |

(Continued)

FOREIGN PATENT DOCUMENTS

WO    WO2014152337    9/2014

*Primary Examiner* — Lynnsy M Summitt
(74) *Attorney, Agent, or Firm* — David Meibos; Maywood IP Law

(57) ABSTRACT

A fusion cage may include an upper endplate directly hinged to a lower endplate. The fusion cage may be adjustable to provide various angles between the endplates. An insert may be coupled between the endplates to lock the endplates at a selected angle. Fasteners may extend through the fusion cage into adjacent bone portions. An instrument may couple to an endplate so that the hinged-together endplates may be inserted between bone portions. The instrument may be used to adjust the angle between the endplates and to couple the insert between the endplates.

12 Claims, 10 Drawing Sheets

(56) References Cited

U.S. PATENT DOCUMENTS

| | | | | |
|---|---|---|---|---|
| 6,454,807 B1* | 9/2002 | Jackson | .................. | A61F 2/447 623/17.15 |
| 6,576,016 B1* | 6/2003 | Hochshuler | ........... | A61F 2/4455 623/17.15 |
| 6,685,742 B1* | 2/2004 | Jackson | .................. | A61F 2/447 623/17.11 |
| 6,962,606 B2* | 11/2005 | Michelson | ............ | A61F 2/4455 623/17.11 |
| 7,637,952 B2* | 12/2009 | Landry | .................. | A61F 2/442 606/100 |
| 8,308,804 B2* | 11/2012 | Krueger | .................. | A61F 2/442 623/17.11 |
| 8,946,706 B2* | 2/2015 | Kim | ....................... | H01L 22/34 257/202 |
| 9,414,932 B2* | 8/2016 | Errico | ..................... | A61F 2/442 |
| 9,526,628 B2* | 12/2016 | Krueger | .................. | A61F 2/442 |
| 9,839,527 B2* | 12/2017 | Robinson | ................ | A61F 2/447 |
| 9,980,825 B2* | 5/2018 | Nichols | ............... | A61F 2/30767 |
| 2003/0233145 A1* | 12/2003 | Landry | ............... | A61B 17/025 623/17.11 |
| 2011/0153020 A1 | 6/2011 | Abdelgany | | |
| 2014/0114420 A1* | 4/2014 | Robinson | ................ | A61F 2/447 623/17.16 |
| 2014/0257486 A1* | 9/2014 | Alheidt | .................. | A61F 2/447 623/17.15 |
| 2014/0309741 A1* | 10/2014 | Ganter | .................... | A61F 2/442 623/17.16 |
| 2015/0223945 A1 | 8/2015 | Weiman | | |
| 2015/0351925 A1* | 12/2015 | Emerick | ................. | A61F 2/447 623/17.16 |
| 2018/0344473 A1* | 12/2018 | Baynham | ................ | A61F 2/442 |

* cited by examiner

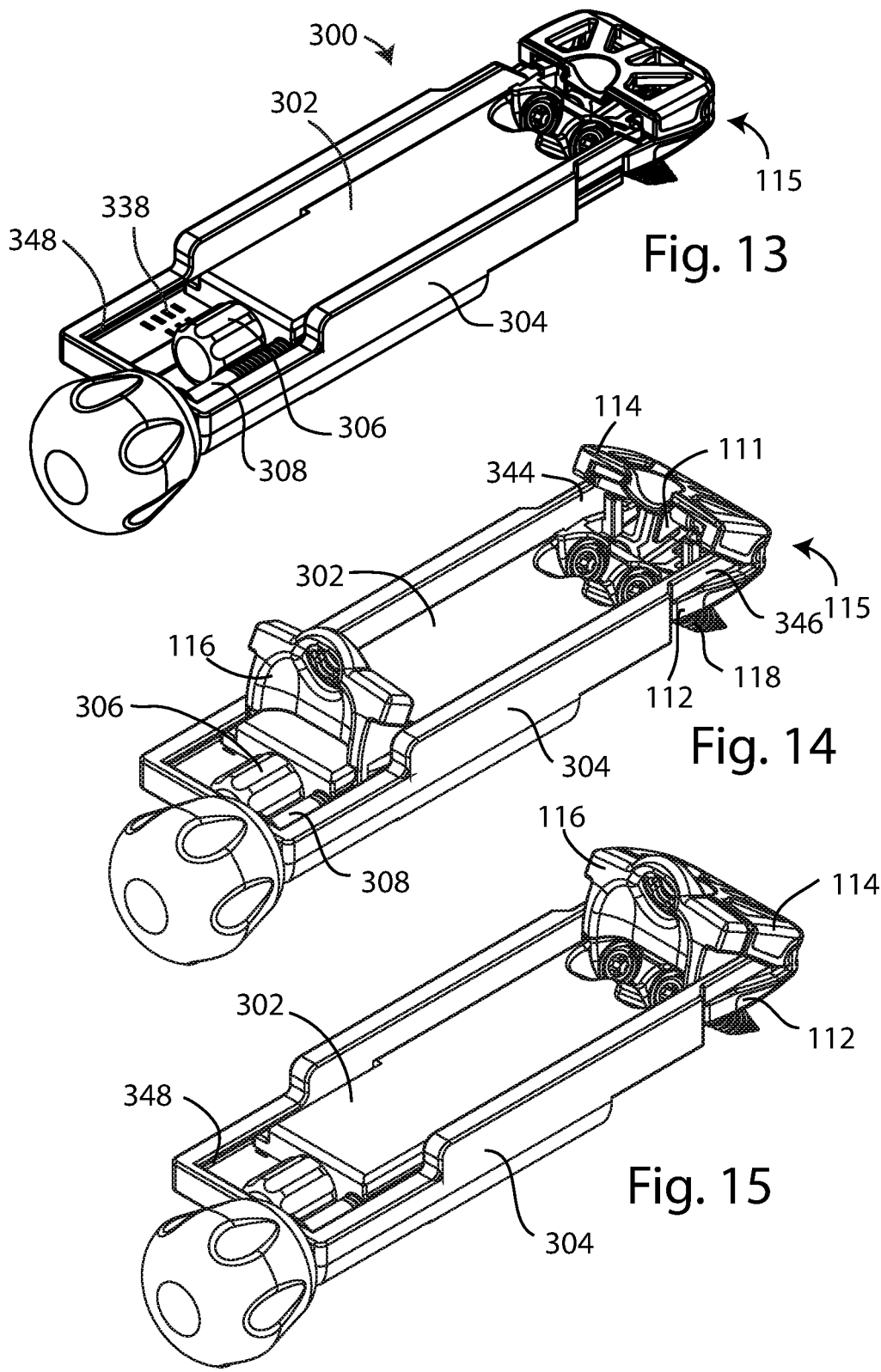

INTERVERTEBRAL CAGE

CROSS-REFERENCE TO RELATED APPLICATIONS

The present application claims the benefit of U.S. Provisional Application Ser. No. 62/410,156, entitled INTERVERTEBRAL CAGE, which was filed on Oct. 19, 2016.

The foregoing is incorporated by reference as though set forth herein in its entirety.

TECHNICAL FIELD

The present disclosure relates to fusion cages for use between bones or bone portions, wherein the cages are adjustable to provide a variable angle between the bones or bone portions. More specifically, the present disclosure relates to adjustably expandable intervertebral fusion cages that provide a variable lordotic angle.

BACKGROUND

In a vertebrate spine, the spinal disc and/or vertebral bodies may be displaced or damaged due to trauma, disease, degenerative defects, or wear over an extended period of time. One result of this displacement or damage to a spinal disc or vertebral body may be chronic back pain. A common procedure for treating damage or disease of the spinal disc or vertebral body may involve partial or complete removal of an intervertebral disc. An implant, which may be referred to as an intervertebral cage or interbody spacer, can be inserted into the cavity created where the intervertebral disc was removed to help maintain height of the spine. An intervertebral cage typically is packed with bone and/or bone-growth-inducing materials to promote fusion between the intervertebral bodies.

One drawback of spacers known in the art is that they can be of fixed height and may not provide adequate height restoration or lordotic correction. In addition, with the design of some existing cages it can be difficult to provide a sufficiently large volume of bone graft for optimal bone regeneration.

Disclosed herein is an intervertebral cage which is adjustably expandable to provide a variable angle of lordotic correction. In some embodiments, the lordotic correction provided may range from 4° to 32°, although any lordotic correction angle may be provided within the scope of the disclosure. The cage includes first and second endplates connected at a hinge feature, which allows the cage to expand widely, creating a large internal space for graft placement. A wedge member is insertable into engagement with the endplates to contain the graft and maintain the cage at the desired degree of expansion for lordotic correction. The endplates may include porous portions for promoting bone in-growth, and openings for bone through-growth between the adjacent vertebral bodies. The cage may be produced using 3D printed titanium. During a method of implantation, an instrument assembly may be deployed to position and hold the endplates, open the endplates to a desired correction angle, and guide the insert into engagement with the endplates to lock the cage at the selected angle. The correction angle may be determined by a practitioner during the implantation procedure. The cage may be directly fastened to the adjacent vertebral bodies. When implanted in a portion of a spine between two adjacent vertebral bodies, the cage disclosed herein may provide deformity correction, restoration of natural sagittal balance, and improved osseointegration.

SUMMARY

The various systems and methods of the present technology have been developed in response to the present state of the art, and in particular, in response to the problems and needs in the art that have not yet been fully solved by currently available fusion cages. The systems and methods of the present technology may provide a fusion cage with an adjustable angle between bone-contacting elements, or endplates, and methods of adjusting and locking the fusion cage in a particular angular orientation.

To achieve the foregoing, and in accordance with the technology as embodied and broadly described herein, an aspect of the technology may include an intervertebral cage, including: a first endplate; a second endplate; and an insert positioned between the first endplate and the second endplate, and directly connected to at least one of the first and second endplates, wherein the insert maintains the position of the second endplate at a selected angle relative to the first endplate.

Embodiments of this aspect of the technology may include any or all of the following attributes. The intervertebral cage may include a hinge joining the first endplate to the second endplate. Each of the first and second endplates includes a porous region to promote bone ingrowth. At least one of the first endplate, the second endplate, and the insert is manufactured by 3D printing. At least one of the first endplate, the second endplate, and the insert, includes titanium. The selected angle is included in the range of 4° to 32°. The insert includes at least one wall bounded by an upper rail and a lower rail, wherein the selected angle is defined as the angle between the upper rail and the lower rail. The intervertebral cage may include a locking mechanism, wherein the locking mechanism locks the insert to the lower endplate. The cage includes an anterior end and a posterior end, wherein the hinge is located at the posterior end. The insert is connected to at least one of the endplates via a dovetail connection.

Another aspect of the technology may include a system for implantation of an intervertebral cage, the system including: an intervertebral cage assembly including a first endplate, second endplate, and an insert which defines an insert angle, the first endplate joined to the second endplate at a pivotable hinge, and the insert positionable between the first and second endplates to support the first endplate relative to the second endplate at a correction angle; an instrument assembly including a distraction structure and an insertion structure, wherein the distraction structure engages at least one of the first endplate and the second endplate to pivot the hinge and position the first endplate relative to the second endplate at the insert angle; wherein the insert is detachably mountable to the instrument assembly and is slidable along the insertion structure and into engagement between and with the first endplate and the second endplate to support the first endplate relative to the second endplate at the correction angle.

Embodiments of this aspect of the technology may include any or all of the following attributes. The insert includes at least one wall bounded by an upper rail and a lower rail, wherein the insert angle is defined as the angle between the upper rail and the lower rail. The insert is chosen from a group of inserts, wherein each insert in the group of inserts defines a different insert angle included in the range of 4° to 32°. The system may include a locking mechanism, wherein the locking mechanism locks the insert to the lower endplate. The insert is mountable to the instrument assembly via a dovetail connection.

Yet another aspect of the technology may include a method for implanting an intervertebral prosthesis between first and second adjacent vertebrae to provide a lordotic correction, the method including: distracting the first and second vertebrae; determining in situ a desired correction angle between the first and second vertebrae; providing a group of intervertebral prostheses, each prosthesis defining a different prosthesis correction angle; selecting an intervertebral prosthesis from the group of intervertebral prostheses, wherein the prosthesis correction angle is equal to the desired correction angle; and implanting the selected intervertebral prosthesis between the first and second adjacent vertebrae to secure the vertebrae at the desired correction angle.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed in this or any other application claiming priority to this application, but is merely representative of exemplary embodiments of the technology. Understanding that these drawings depict only exemplary embodiments and are, therefore, not to be considered limiting of the scope of the technology, the exemplary embodiments will be described with additional specificity and detail through use of the accompanying drawings in which:

FIG. 13 is a perspective view of the instrument assembly of FIG. 11A positioning the intervertebral cage endplates;

FIG. 14 is a perspective view of the instrument assembly of FIG. 11A distracting the intervertebral cage endplates;

FIG. 15 is a perspective view of the instrument assembly of FIG. 11A with the insert member guided into engagement with the intervertebral cage endplates.

DETAILED DESCRIPTION

Figure 1:
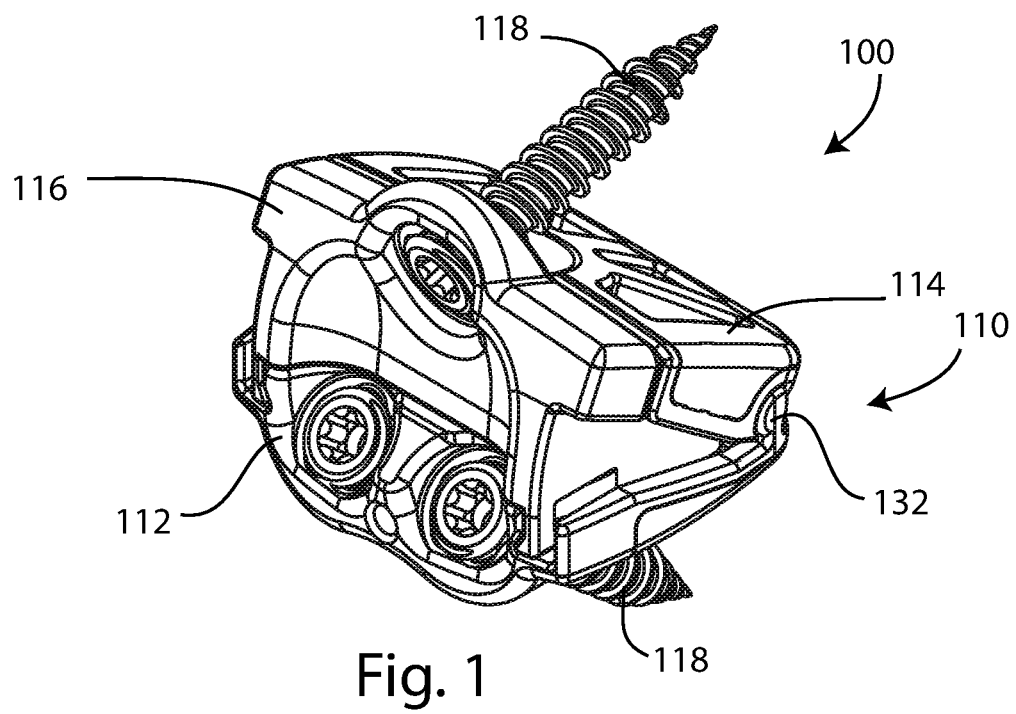
FIG. 1 is an isometric view of an intervertebral cage assembly comprising first and second endplates, an insert member, and a plurality of fastening members.
Figure 2:
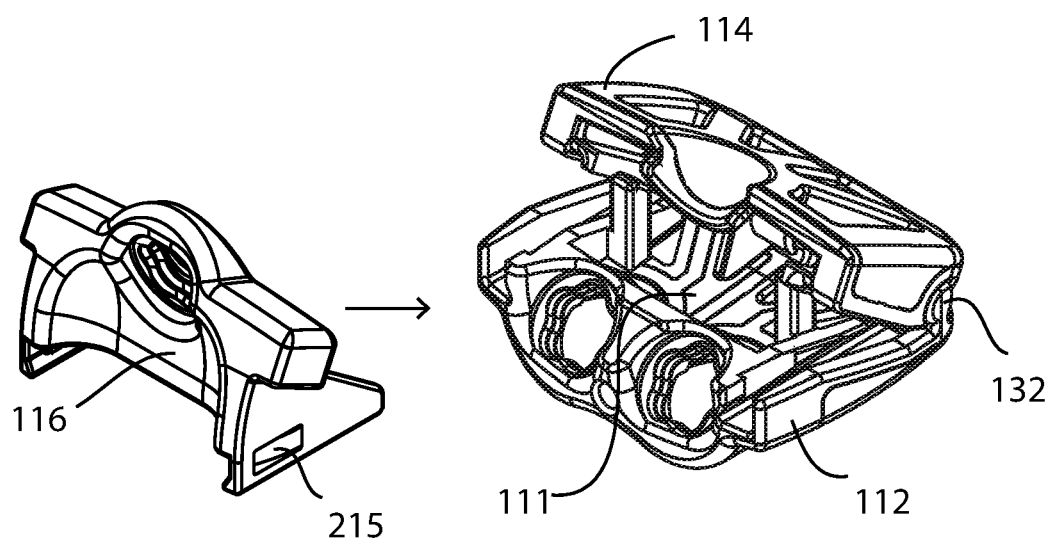
FIG. 2 is a partially exploded view of the upper and lower endplates and insert member of the intervertebral cage assembly of FIG. 1.
Figure 3:
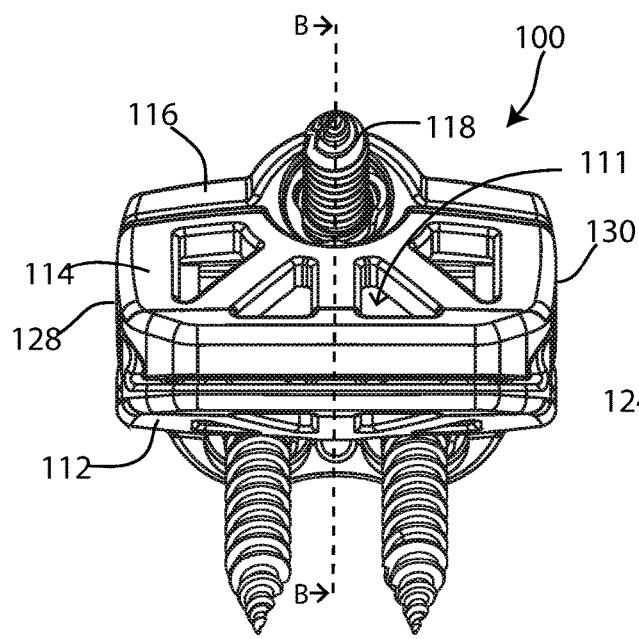
FIG. 3 is a rear or posterior view of the intervertebral cage assembly of FIG. 1.
Figure 4:
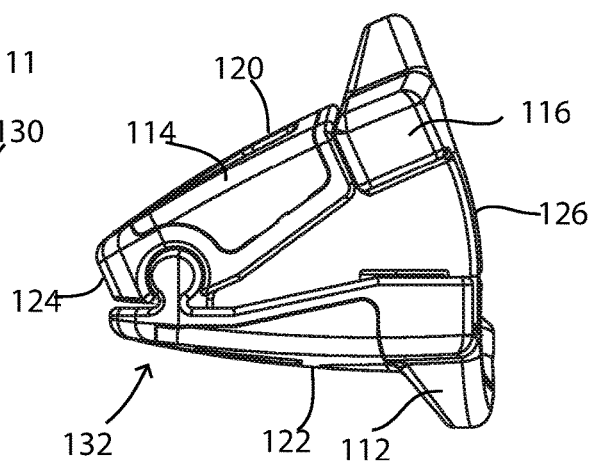
FIG. 4 is a right side view of the upper and lower endplates and insert member of the intervertebral cage assembly of FIG. 1.
Figure 5:
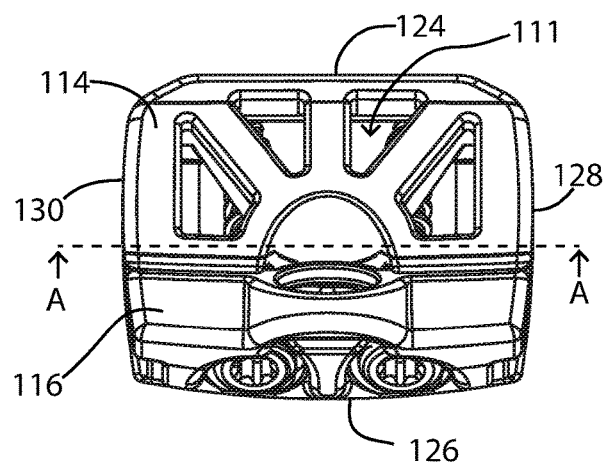
FIG. 5 is a top view of the intervertebral cage assembly of FIG. 1, an upper fastening member omitted.
Figure 6:
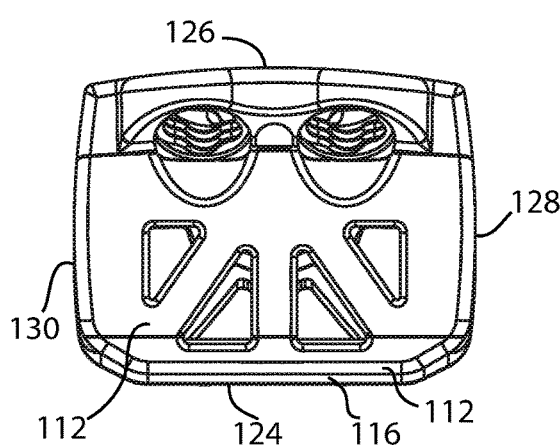
FIG. 6 is a bottom view of the intervertebral cage assembly of FIG. 1, with the fastening members omitted.

Referring to FIGS. 1-10E, an intervertebral cage assembly 100 of the disclosure includes an intervertebral cage 110 comprising a first endplate 112 which may be a lower endplate, a second endplate 114 which may be an upper endplate; and an insert 116 which may be a wedge member. An internal or interior space 111 is bounded by the endplates 112, 114 and the insert 116. The assembly may further comprise at least one fastener for affixing the intervertebral cage to one or more vertebral bodies. The illustrated fasteners are screws 118; other embodiments may include different fasteners or no fasteners. With reference to FIGS. 3 and 4, the intervertebral cage 100 may include a superior side 120, an inferior side 122, a posterior end or leading end 124, an anterior end or trailing end 126, and left and right lateral sides 128, 130. It is understood that the terms upper, lower, superior, inferior, anterior, posterior, right, and left, are used as relative terms with reference to an implant of the present disclosure as implanted from an anterior approach into a portion of a spine between two adjacent vertebral bodies. In other embodiments within the scope of the disclosure, the intervertebral cage disclosed herein could be implanted in different orientations and/or from different approaches.

Figure 7A:
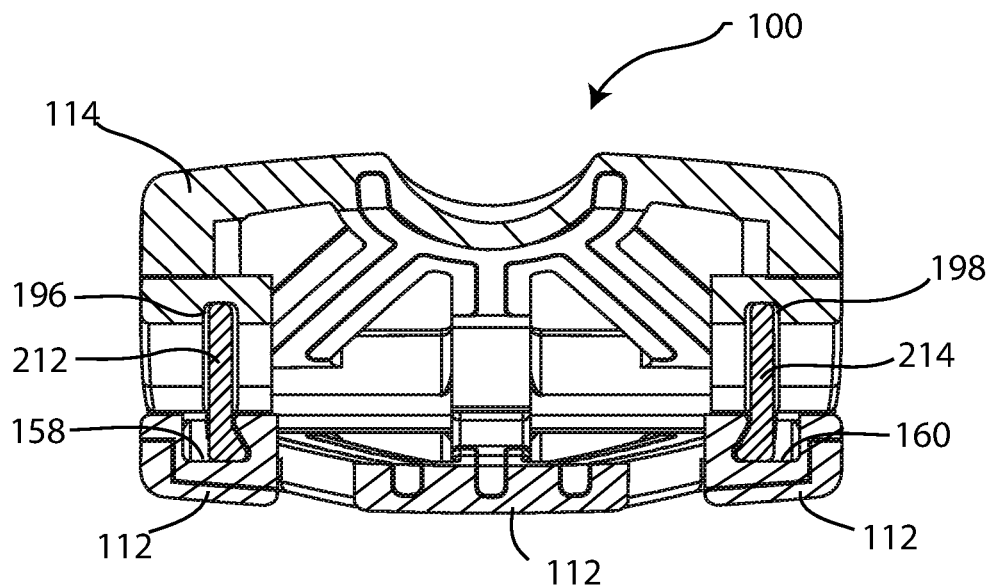
FIG. 7A is a coronal cross-sectional view of the intervertebral cage assembly of FIG. 1, taken along line A-A in FIG. 5.
Figure 7B:
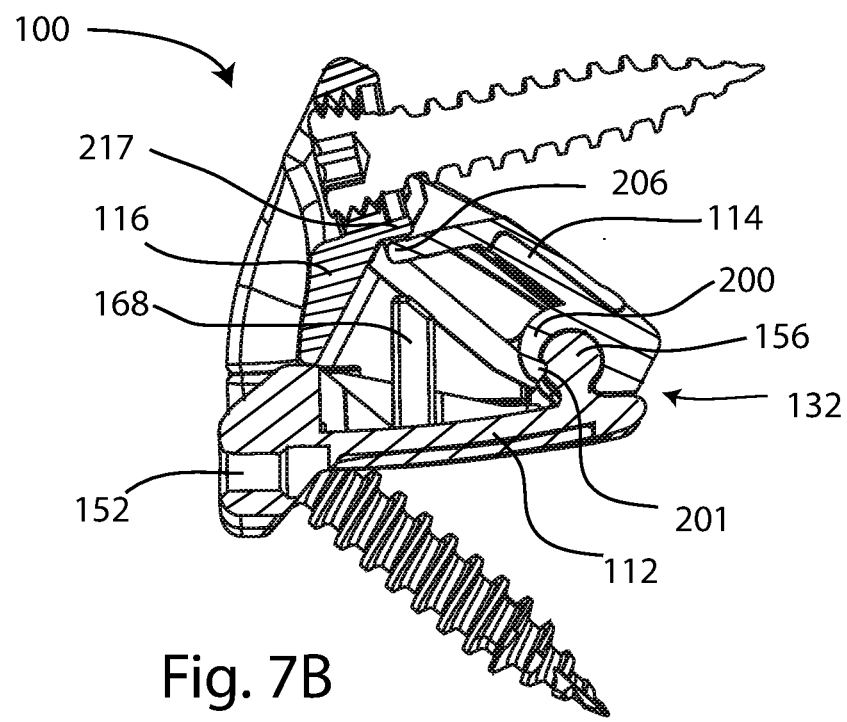
FIG. 7B is a sagittal cross-sectional view of the intervertebral cage assembly of FIG. 1, taken along line B-B in FIG. 3.
Figure 8A:
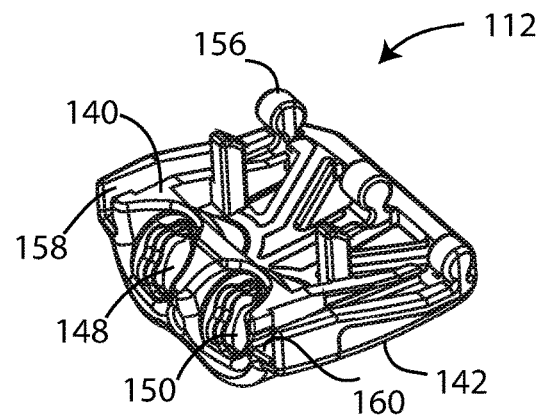
FIG. 8A is an isometric view of the first endplate of the intervertebral cage assembly of FIG. 1.
Figure 8B:
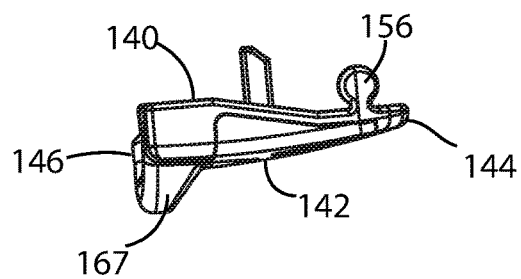
FIG. 8B is a left side view of the first endplate.
Figure 8C:
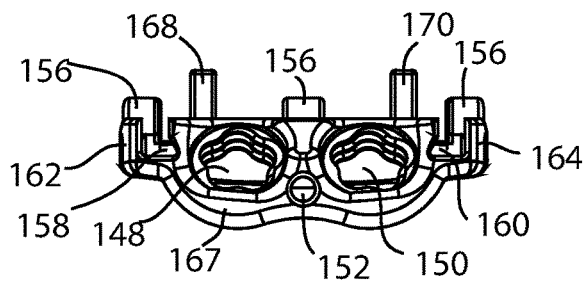
FIG. 8C is a front or anterior view of the first endplate.
Figure 8D:
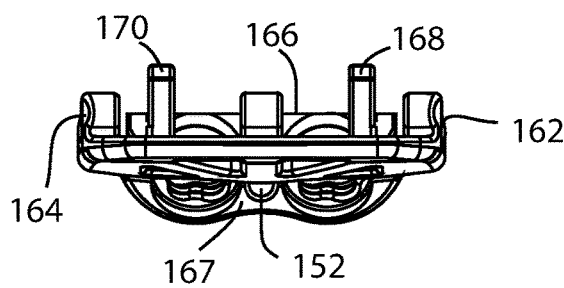
FIG. 8D is a rear view of the first endplate.
Figure 8E:
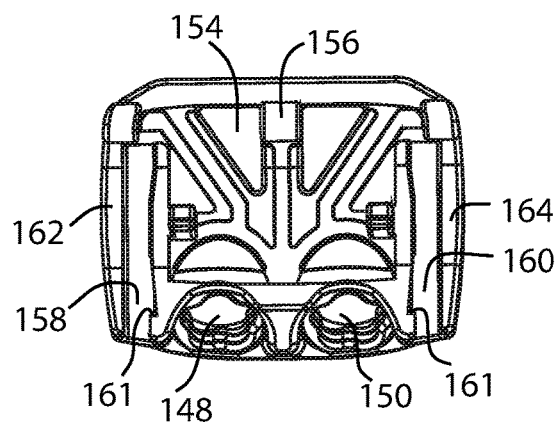
FIG. 8E is a top view of the first endplate.
Figure 8F:
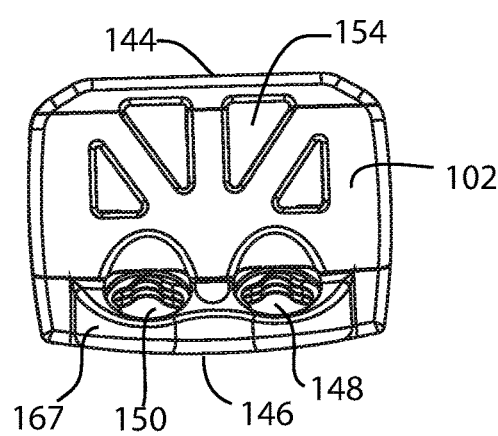
FIG. 8F is a bottom view of the first endplate.
Figure 9A:
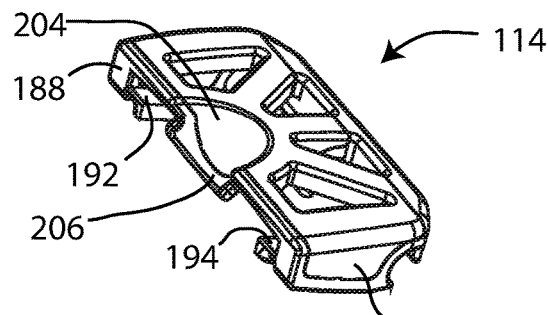
FIG. 9A is an isometric view of the second endplate of the intervertebral cage assembly of FIG. 1.
Figure 9B:
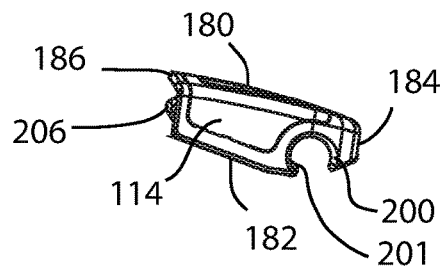
FIG. 9B is a left side view of the second endplate.
Figure 9C:
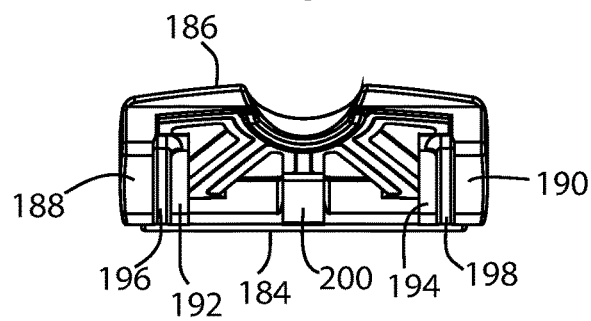
FIG. 9C is a front view of the second endplate.
Figure 9D:
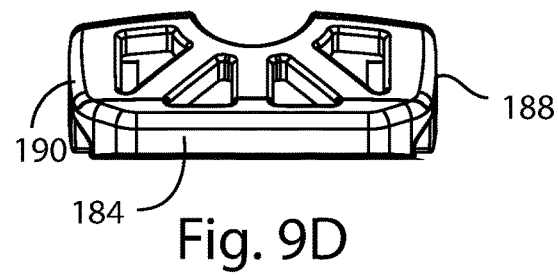
FIG. 9D is a rear view of the second endplate.
Figure 9E:
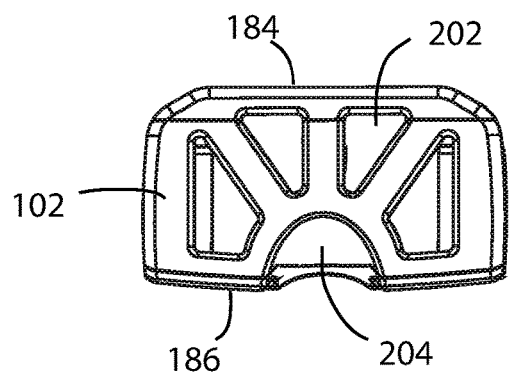
FIG. 9E is a top view of the second endplate.
Figure 9F:
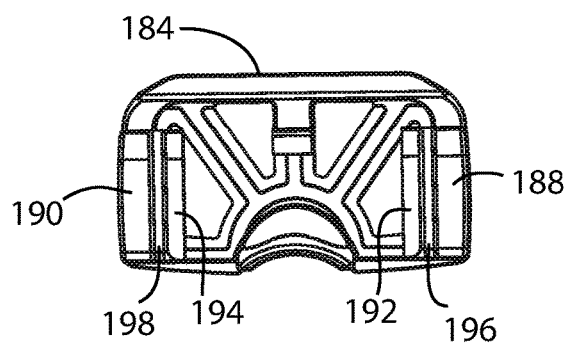
FIG. 9F is a bottom view of the second endplate.
Figure 10A:
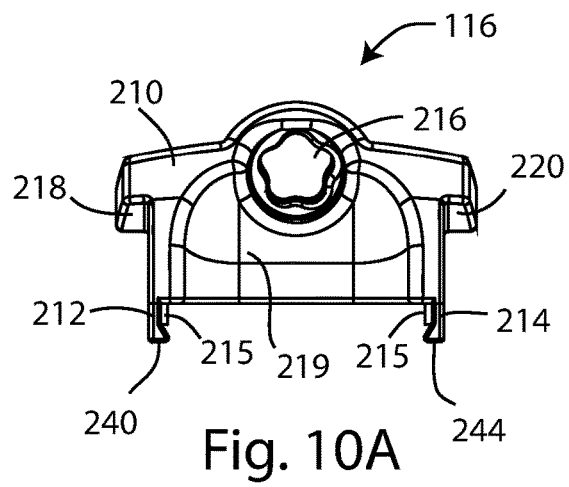
FIG. 10A is a front view of the insert of the intervertebral cage assembly of FIG. 1.
Figure 10B:
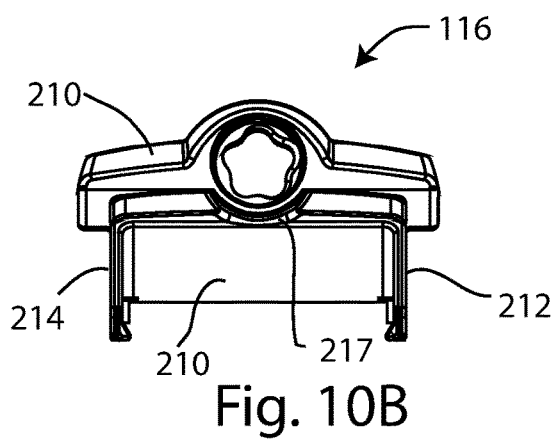
FIG. 10B is a rear view of the insert.
Figure 10C:
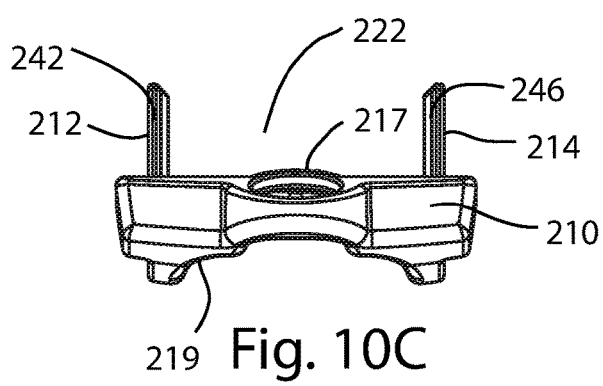
FIG. 10C is a top view of the insert.
Figure 10D:
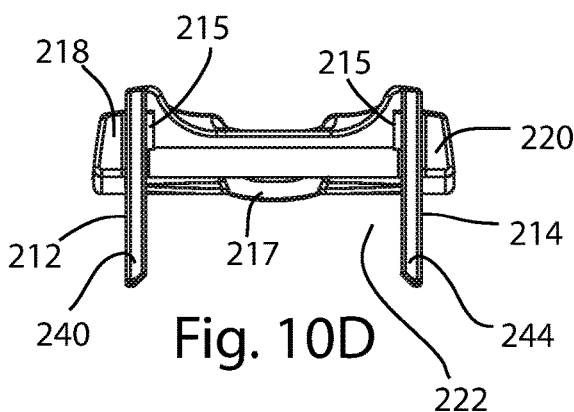
FIG. 10D is a bottom view of the insert.
Figure 10E:
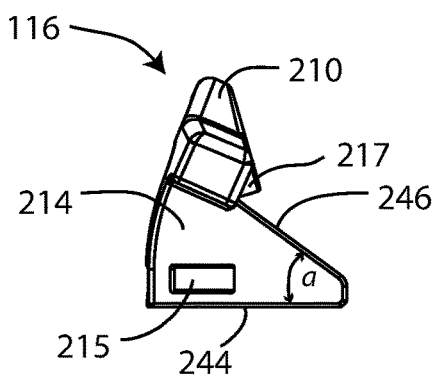
FIG. 10E is a left side view of the insert.
Figure 11A:
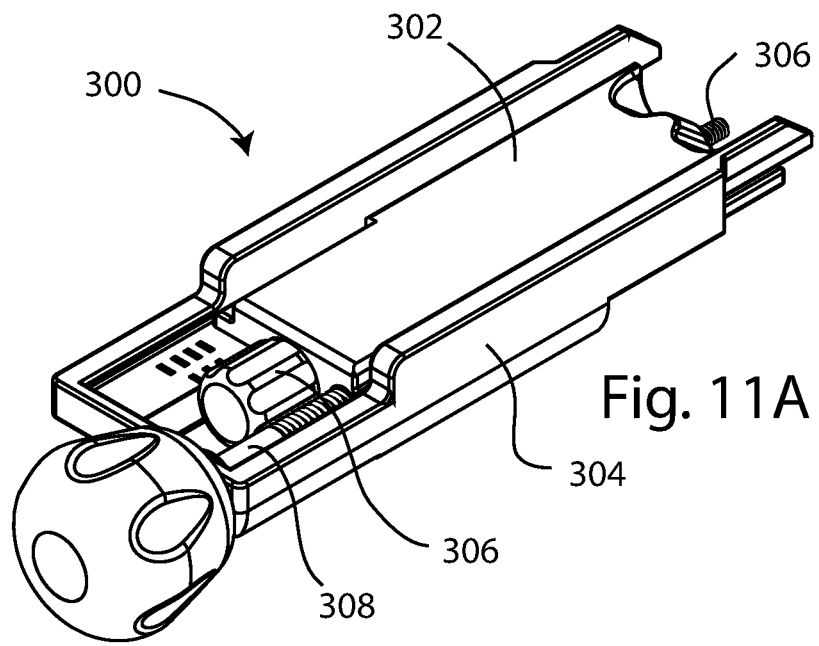
FIG. 11A is an isometric view of an instrument assembly for use with the intervertebral cage assembly of FIG. 1.
Figure 11B:
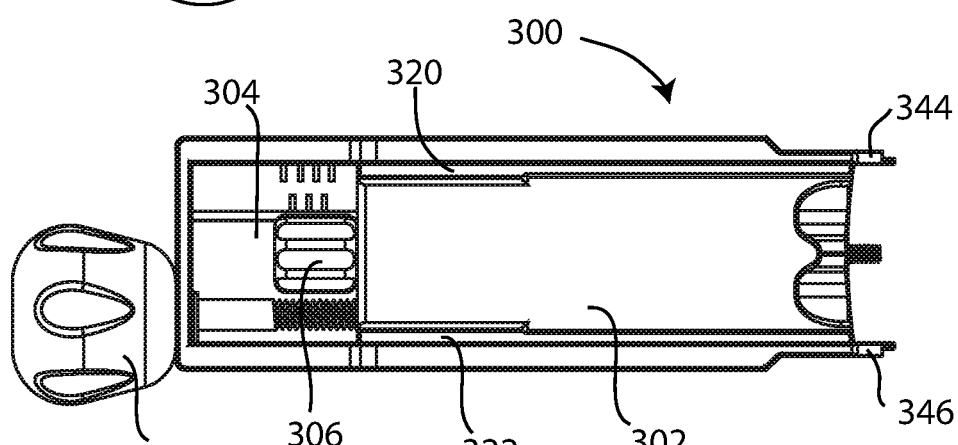
FIG. 11B is a top view of the instrument assembly of FIG. 11A.
Figure 11C:
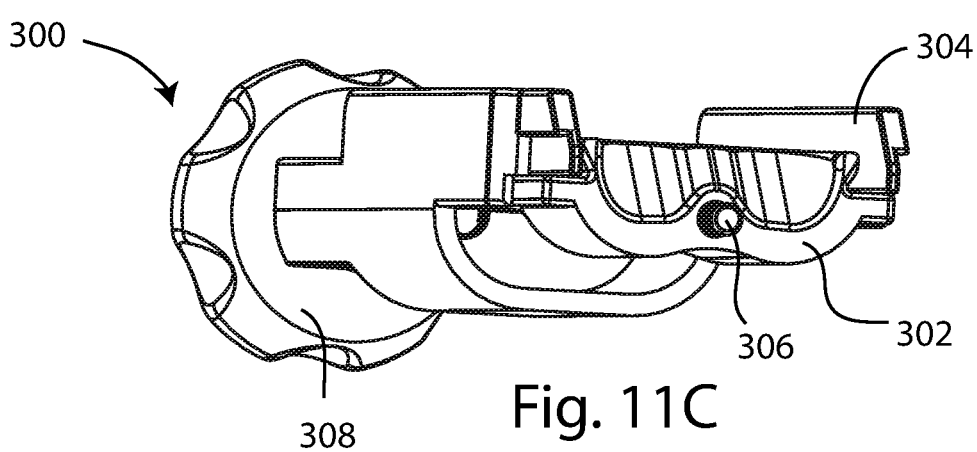
FIG. 11C is a perspective end view of the instrument assembly of FIG. 11A.

As seen in FIGS. 1, 2 and 4, the upper and lower endplates 112, 114 are directly connected to each other at a hinge 132, forming an endplate assembly 115. The endplates may open away from one another to a desired correction angle or lordotic angle; in FIGS. 1, 2 and 4 the angle shown is 28°. The insert 116 is slidable into direct engagement with the upper endplate 112 and/or lower endplate 114, locking the juxtaposition of the endplates at the selected correction angle, as seen in FIG. 7B. In an embodiment, the illustrated endplates can be implanted without the addition of an insert; in that embodiment the built in correction angle is 4°. In the embodiment depicted, the intervertebral cage 110 and each of its constituent components 112, 114 and 116 are bilaterally symmetrical relative to a midline sagittal plane extending between the posterior and anterior ends 124, 126.

The superior and inferior sides 120, 122 of the cage 100 as depicted are slightly rounded or domed both anterior-posteriorly and medial-laterally for mating contact with vertebral endplate surfaces. Other embodiments can include flattened surfaces, and/or posts, serrations, teeth, pegs, or surface roughening in order to enhance contact and engagement with the vertebral endplates. Selected regions of each of the superior and inferior sides may be formed of and/or coated with porous material 102 such as porous titanium, to promote bone ingrowth.

Referring to FIGS. 8A-8F, additional views of the lower endplate 112 are shown. Lower endplate 112 is generally rectangular in footprint when viewed from a superior or inferior perspective as in FIGS. 8E and 8F. The lower endplate includes a superior side 140, an inferior side 142, a posterior end 144 and an anterior end 146. First and second holes 148, 150 open through the endplate 112 to receive fasteners 118. In some embodiments the holes may be tapped or threaded; in some embodiments one or more of the holes may be non-threaded; in some embodiments the hole may comprise a spherical socket. Other embodiments of the engagement may exclude fasteners and/or fastener holes. A counterbore or concavity may surround the holes 148, 150 to enable a screw head to be recessed into the cage. A bore 152 extends at least partially into the lower endplate 112 between the holes 148, 150 for engagement with implantation instrumentation. At least one opening 154 extending through the endplate 112 between the superior and inferior sides 140, 142 may be present to promote bone through-growth. Four openings 154 are illustrated. Openings 154 may occupy a substantial area of the inferior side 142 of the endplate 112 in order to allow maximal area for bone through-growth.

At least one hinge knuckle 156 protrudes from the lower endplate 112 to form a hinge connection with the upper endplate 114. In the embodiment depicted, three hinge knuckles are included; in other embodiments fewer or more hinge knuckles may be present, or a single continuous hinge knuckle may extend between the lateral sides of the endplate. Some embodiments may include other types of hinges; for example a slot or groove which receives a pin, such as a piano or door hinge. Having less space devoted to the hinge connection can allow additional volume for bone graft and subsequent bone ingrowth. Having a hinge connection that is integrally formed with the endplates 112, 114 so that the endplates are directly connected may increase hinge strength and/or reduce hinge size to allow more room for bone graft and/or bone ingrowth. Furthermore, the endplates 112, 114 with integrally formed hinge connection may be fabricated together simultaneously, for example by an additive manufacturing process such as 3D printing. In this arrangement, the hinge connection may be formed so that it is free to articulate but cannot be disassembled under service conditions. Parasagittally located first and second slots 158, 160 extend across the endplate 112 in an anterior-posterior orientation. The slots include an undercut feature to form a dovetail connection with the insert 116, and a dovetail connection with insertion instrumentation. Other embodiments within the scope of the disclosure could include one slot, or more than two slots; in other embodiments slots may be centrally or parasagittally located. A catch 161 or tooth may be formed adjacent each of the slots to aid in retention of the insert 116. First and second sidewalls 162, 164 project superiorly and form the lateral edges of the endplate 112. A raised portion 166 of the endplate 112 projects superiorly and connects to a lip portion 167 which projects inferiorly; the fastener holes 148, 150 may be housed in the raised portion and the lip. First and second posts 168, 170 project superiorly from the endplate 112 and may assist in retaining the insert 116. The posts may prevent unintentional lateral disassembly of the cage; the posts may be excluded from other embodiments of the endplate.

Referring to FIGS. 9A-9F, additional views of the upper endplate 114 are shown. Upper endplate 114 is generally rectangular in footprint when viewed from a superior or inferior perspective as in FIGS. 9E and 9F. The lower endplate includes a superior side 180, an inferior side 182, a posterior end 184 and an anterior end 186. First and second sidewalls 188, 190 extend anterior-posteriorly along the lateral edges of the endplate 114. A first flange 192 or shelf projects inwardly from the first sidewall 188, and a second flange 194 or shelf projects inwardly from the second sidewall 190. First and second grooves 196, 198 are formed in the first and second flanges 192, 194 respectively, and receive standing sidewalls of the insert 116 (discussed below) when the insert is guided into engagement with the endplates. One or more receivers 200 are located toward the posterior end 184 to mate with the hinge knuckles 156 to form the hinge 132. At least one protrusion 201 may be formed on at least one receiver 200, for example on an interior surface of the receiver. See FIG. 7B. The protrusion 201 interferes with the mating hinge knuckle on the other endplate, creating friction to provide resistance or drag to keep the hinge in its selected position. One or more openings 202 extends through the endplate 114 between the superior and inferior sides 180, 182 to promote bone through-growth. A recess 204 may be depressed into the endplate 114 to provide passage for a fastener. A rim 206 projects anteriorly from the endplate 114 and may complementarily engage with a feature on the insert 116. Openings 202 may occupy a substantial area of the superior side 180 of the endplate 114 in order to allow maximal area for bone through-growth.

It is appreciated that in other embodiments within the scope of the disclosure, one or more features of the upper and lower endplates 112, 114 may be reversed or swapped from one endplate to the other. By way of non-limiting example, hinge knuckles and receivers may be reversed or swapped, fastener-receiving features may be reversed or swapped, or features complementary to the insert 116 may be reversed or swapped.

Referring to FIGS. 10A-10E, additional views of the insert 116 are shown. Insert 116 is generally wedge-shaped when viewed from a lateral perspective as in FIG. 10E, which is a view of the left side of the insert. Insert 116 is generally open-ended in a posterior direction, having an anterior end wall 210 flanked parasagittally by a first sidewall 212 and a second sidewall 214. The sidewalls 212, 214 extend posteriorly from the end wall 210. First sidewall 212 is bounded by a lower rail 240 and an upper rail 242; the upper and lower rails define an insert angle $\alpha$ between them. Similarly, the second sidewall 214 is bounded by a lower rail 244 and an upper rail 246; the upper and lower rails define the angle $\alpha$ between them. FIGS. 16A-16F depict inserts having differing insert angles ranging from 8° to 32°.

Although the inserts depicted include insert angles differing by 4° intervals, it is appreciated that an insert within the scope of the disclosure could define any angle desired. Each insert sidewall 212, 214 is generally triangular in shape when viewed from the side, to provide the wedge shape for lordotic correction. When assembled with lower endplate 112, lower rails 240, 244 are received in slots 158, 160 in a dovetail connection. When assembled with upper endplate 114, upper rails 242, 246 are received in the grooves 196, 198. See FIG. 7A.

Between the end wall 210 and sidewalls 212, 214 is a wide gap 222, which contributes to the space available for bone graft material. The end wall 210 includes a hole 216 for passage of a fastener; the hole may be non-threaded or include threads, tapping or ridges for engagement with a fastener head. Other embodiments of the insert and/or endplates may exclude fastener holes. A counterbore or concavity may surround the hole 216 to enable a screw head to be recessed into the end wall of the insert. A boss 217 may project posteriorly from the end wall and may engage the rim 206 of the upper end plate 114 when the implant 100 is assembled. See FIG. 7B. The end wall 210 may further house an anterior concavity or hollow portion 219. A first projection 218 and a second projection 220 may extend laterally from the superior end of the end wall 210 and may align continuously with the upper endplate 114 sidewalls 188, 190 when the cage 110 is properly assembled, as seen in FIG. 4.

A tab 215 may project inwardly from each sidewall 212, 214 for engagement with the catches 161 on the lower endplate 112, forming a locking mechanism 230 to retain the insert. Of course, it is understood that the locations of the catches and tabs may be reversed; or the catches and/or tabs may be formed on the upper endplate; or an embodiment may include no catch/tab retention feature or another type of retention feature known in the art. Other features of the insert 116 may also be reversed, for example, swapped between a superior and inferior location.

The endplates 112, 114 may be connected to form cage 110, as shown in FIGS. 1, 4, 7A and 7B. The insert 116 is directly and positively fixed to the lower endplate 112 via the locking mechanism described previously. The boss 217 on the insert 116 overhangs the rim 206 of the upper endplate 114, engaging the insert with the upper endplate and further locking the positions of the upper and lower endplates with respect to one another, providing the desired correction angle. In the embodiment depicted, if no insert 116 were included, the cage 110 alone provides a lordotic correction angle of 4°. Other embodiments of the cage within the scope of the disclosure may provide a correction angle ranging from 0° to 4°, or greater than 4°. When an insert 116 is properly engaged with cage 110 as in FIG. 1, the total correction angle provided is 4° plus the insert angle. This arrangement allows for maximum graft packing within the interior space formed between the insert and the endplates. In other embodiments of the disclosure, the insert 116 may be positively fixed to both the upper and lower endplates, to either endplate, or to neither.

Referring to FIGS. 11A-15, an instrument assembly 300 may be employed to retain cage 110 and insert it between two adjacent vertebral bodies. Instrument assembly 300 includes an insertion structure 302 slidingly engaged with a distraction structure 304. A draw bar 306 extends longitudinally through the insertion structure 302. A trialing shaft 308 extends through the distraction structure 304 and is threadably engaged with the insertion structure 302.

Figure 12:
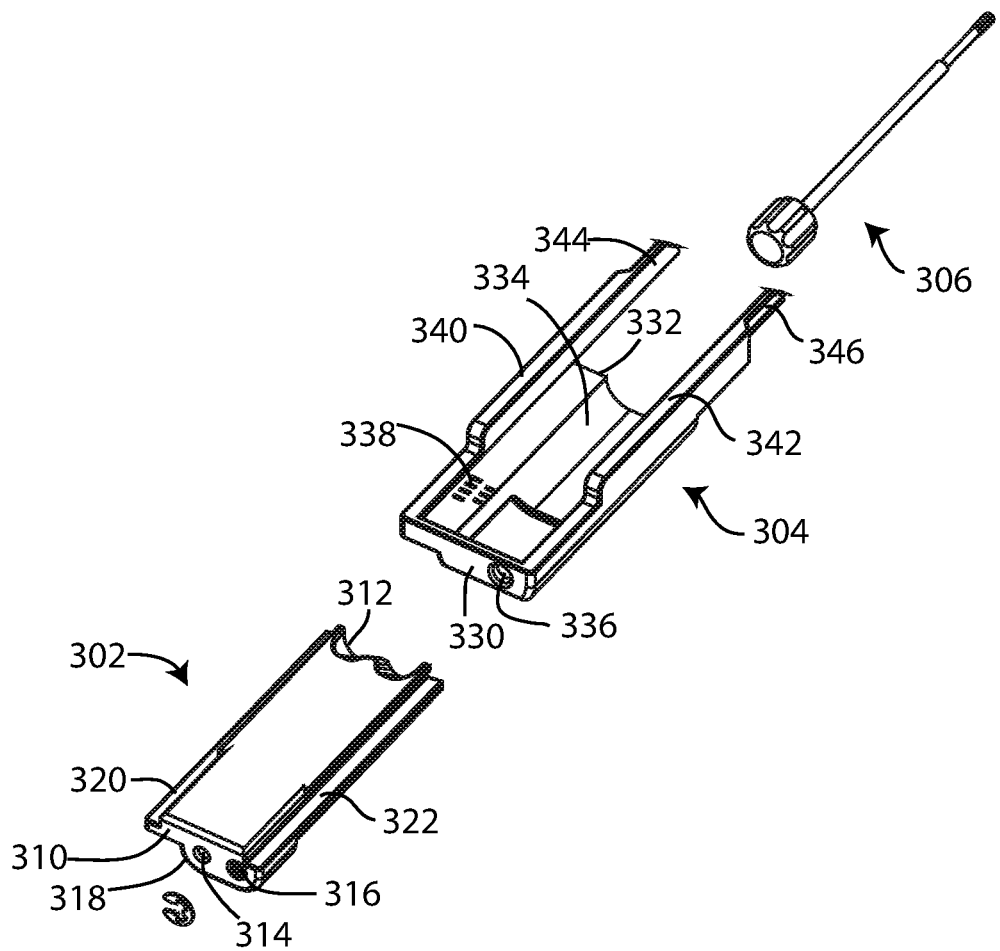
FIG. 12 is an exploded isometric view of the instrument assembly of FIG. 11A.
Figure 16A:
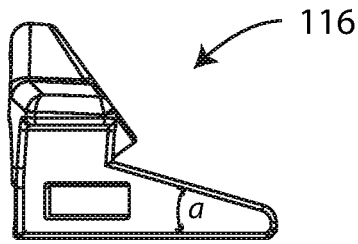
FIG. 16A is a left side view of an insert member comprising an 8° correction angle.
Figure 16D:
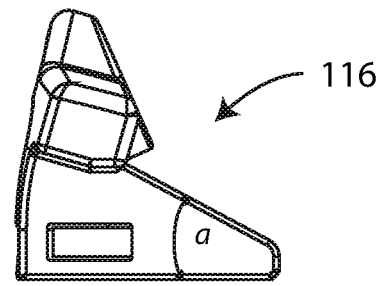
FIG. 16D is a left side view of an insert member comprising a 20° correction angle.
Figure 16B:
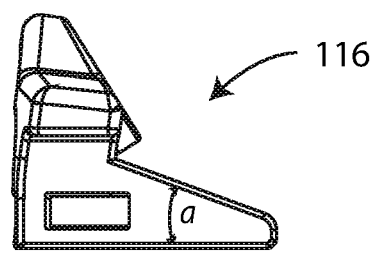
FIG. 16B is a left side view of an insert member comprising a 12° correction angle.
Figure 16E:
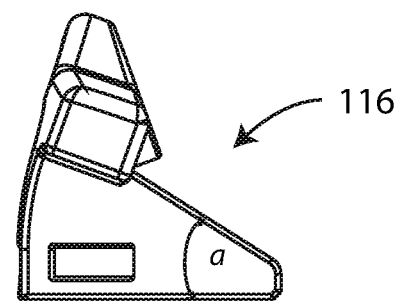
FIG. 16E is a left side view of an insert member comprising a 24° correction angle.
Figure 16C:
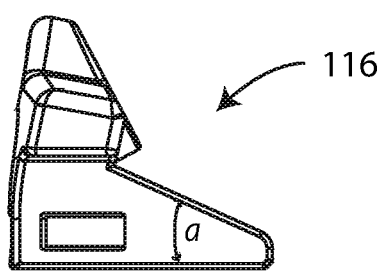
FIG. 16C is a left side view of an insert member comprising a 16° correction angle.
Figure 16F:
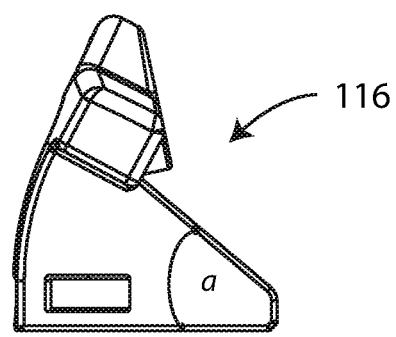
FIG. 16F is a left side view of an insert member comprising a 32° correction angle.

Referring to FIG. 12, the insertion structure 302 extends longitudinally between a proximal end 310 and a distal end 312. A first bore 314 extends longitudinally through the structure 302 for passage of the draw bar 306. The first bore 314 may include an internally threaded portion that may be recessed from the distal end 312; the rest of the first bore 314 may be smooth. The internally threaded portion of the first bore 314 may threadedly engage an externally threaded distal portion of the draw bar 306. The distal portion of the draw bar 306 may be threaded completely past the internally threaded portion of the first bore 314 so that the threads are disengaged and the distal portion of the draw bar 306 protrudes distally past the distal end 312 of the insertion structure 302. See FIGS. 11A-11C. In this state, the internal threads of the first bore 314 and the external threads of the draw bar 306 may prevent unintentional disassembly and/or withdrawal of the draw bar from the insertion structure. A second bore 316 extends into the proximal end 310 of the structure 302 for retention of the trialing shaft 308. The second bore 316 may be internally threaded over most or all of its length. An inferior surface 318 of the insertion structure 302 is shaped to complementarily fit with the distraction structure 304. First and second tracks 320, 322 extend along the longitudinal edges of the insertion structure.

The distraction structure 304 extends longitudinally between a proximal end 330 and a distal end 332. A superior surface 334 of the structure between the proximal and distal ends is shaped to complementarily receive the inferior surface of the insertion structure, and allow smooth sliding of the insertion structure relative to the distraction structure. A hole 336 in the proximal end aligns with the bore 316 of the insertion structure 302 when the instrument assembly 300 is assembled, allowing passage of the trialing shaft 308. Indicia 338 may be present to indicate the distraction angle. A series of staggered lines is shown; text may also be included. Raised sidewalls 340, 342 project superiorly and distally from the proximal portion of the distraction structure 304, forming first and second prongs 344, 346 or arms. First and second undercuts 348, 350 extend longitudinally between the proximal and distal ends of the distraction structure, inferior to the raised sidewalls. The undercuts 348, 350 may be rectangular or square grooves. See FIGS. 13 and 15; undercut 350 is not visible.

One method of implantation of intervertebral cage assembly 100 is described with reference to FIGS. 13-15. Referring to FIG. 13, the upper 114 and lower 112 endplates are hinged together to form the endplate assembly 115 which is mounted on the distal end of instrument assembly 300, with draw bar 306 engaged in bore 152 of the lower endplate 112. The draw bar 306 may thread into the bore 152. The first and second prongs 344, 346 of the distraction structure 304 are received in the first and second slots 158, 160, respectively, of the lower endplate 112. The distal end 312 of the insertion structure 302 abuts the anterior end 146 of the lower endplate 112. Thus retained, the endplate assembly 115 is inserted into the intervertebral space, and one or more screws 118 may be driven through holes 148, 150 to attach the endplate assembly 115 to the lower vertebral body.

Referring to FIG. 14, the trialing shaft 308 is rotated to slidingly push the distraction structure 304 distally with respect to the insertion structure 302, or this may be described as slidingly pulling the insertion structure proximally relative to the distraction structure, due to threaded engagement between the distal portion of the trialing shaft 308 and the second bore 316 of the insertion structure 302.

The proximal portion of the trialing shaft 308 abuts the proximal end 330 of the distraction structure 304.

As the trialing shaft 308 pulls the insertion structure 302 proximally, the first and second tracks 320, 322 of the insertion structure slide proximally within the first and second undercuts 348, 350 of the distraction structure 304. The slots 158, 160 of the cage assembly 115 slide proximally on the prongs 344, 346 of the distraction structure 304 until the prong ends directly contact the inferior aspect of the first and second sidewalls 188, 190 of the upper endplate 114. As the trialing shaft 308 pulls the insertion structure 302 farther proximally, the prong ends push against the sidewalls 188, 190, distracting the upper endplate 114 away from the lower endplate 112. The endplates may be distracted or collapsed by turning the trialing shaft 308 clockwise or counterclockwise, increasing or reducing the angle between the endplates until the desired degree of distraction (or lordotic angle) is reached. The juxtaposition of the insertion structure 302 relative to the indicia 338 on the distraction structure 304 may indicate when the distraction angle (lordotic angle) is attained, or may indicate the magnitude of the lordotic angle achieved. In the embodiment depicted in FIGS. 14-15, insert 116 with the endplates 112, 114 define a correction angle of 32°.

Once the practitioner determines that the desired distraction angle has been achieved, the appropriately sized wedge insert 116, if any, is selected. Insert 116 slides inferiorly into the proximal portion of the distraction structure 304, then slides distally onto the proximal end of the insertion structure 302. Lower rails 240, 244 of the insert 116 are received longitudinally in the tracks 320, 322 of the insertion structure 302 in a dovetail connection, and are held in longitudinal alignment by the sidewalls 340, 342 of the distraction structure. Prior to insertion of the insert 116 into the endplate assembly 115, bone graft material may be packed in the interior space 111 of the endplate assembly 115, and/or gap 222 between the sidewalls 212, 214 of the insert 116.

Referring to FIG. 15, the insert 116 slides distally along the tracks 320, 322 of the insertion structure 302 toward the endplate assembly 115 until the insert lower rails 240, 244 are in engagement with the slots 158, 160 of the lower endplate 112 in a dovetail connection, and insert upper rails 242, 246 are received in the grooves 196, 198 of the upper endplate 114, as in FIG. 7. A tool (not shown) may engage the anterior aspect of the insert to push the insert distally. It is noted that each slot 158, 160 is sufficiently wide to accommodate both an insert sidewall 212 or 214 and distraction structure prong 344 or 346 simultaneously. When the insert 116 is inserted sufficiently distally into the endplate assembly 115, the tabs 215 may engage in the catches 161, thus locking the insert 116 to the lower endplate 112. The boss 217 on the insert 116 may engage with the upper endplate rim 206 to further secure the endplates and insert together and prevent pivoting of the upper endplate relative to the lower endplate. A screw 118 may be driven through hole 216 to fasten the cage 110 to the upper vertebral body.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The terms "upper" and "lower", and "top" and "bottom" are used as relative terms herein for ease of description and understanding. It is understood that in embodiments of the disclosure, upper and lower entities may be reversed.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

The invention claimed is:

1. An intervertebral cage, comprising:
 a first endplate comprising a first vertebra-facing side, an opposite first insert-facing side, a first anterior side, an opposite first posterior side, a first right side, an opposite first left side, and a hinge knuckle protruding from the first insert-facing side;
 a second endplate comprising a second vertebra-facing side, an opposite second insert-facing side, a second anterior side, an opposite second posterior side, a second right side, an opposite second left side, and a receiver formed in the second insert-facing side;

wherein the hinge knuckle protrudes from the first insert-facing side toward the second endplate, wherein the hinge knuckle is received in the receiver to form a hinge between the first and second endplates, wherein the hinge knuckle pivots within the receiver about a hinge axis that extends along a right-left direction so that the first endplate pivots relative to the second endplate about the hinge axis; and an insert positioned between the first endplate and the second endplate, and directly connected to at least one of the first and second endplates, wherein the insert maintains the position of the second endplate at a selected angle relative to the first endplate, wherein the insert is non-adjustable and monolithic, wherein the insert forms at least a portion of an anterior side of the intervertebral cage and at least a portion of a superior side of the intervertebral cage when the insert and the first and second endplates are assembled together.

2. The intervertebral cage of claim 1, wherein the first and second endplates are fabricated together simultaneously so that the hinge is free to pivot and cannot be disassembled under service conditions.

3. The intervertebral cage of claim 1, wherein the selected angle is included in the range of 4° to 32°.

4. The intervertebral cage of claim 1, wherein the intervertebral cage includes an anterior end comprising the first and second anterior sides and a posterior end comprising the first and second posterior sides, wherein the hinge is located at the posterior end.

5. A system for implantation of an intervertebral cage, the system comprising:

an intervertebral cage assembly comprising a first endplate, second endplate, and an insert which defines an insert angle, the first endplate joined to the second endplate at a pivotable hinge, and the insert positionable between the first and second endplates to support the first endplate relative to the second endplate at a correction angle;

wherein the first endplate comprises a hinge knuckle that protrudes from a first insert-facing side of the first endplate toward the second endplate, wherein the second endplate comprises a receiver formed in a second insert-facing side of the second endplate, wherein the hinge knuckle pivots within the receiver to form the hinge; and an instrument assembly comprising a distraction structure and an insertion structure, wherein the distraction structure engages at least one of the first endplate and the second endplate to pivot the hinge and position the first endplate relative to the second endplate at the insert angle;

wherein the insert is detachably mountable to the instrument assembly and is slidable along the insertion structure and into engagement between and with the first endplate and the second endplate to support the first endplate relative to the second endplate at the correction angle.

6. The system of claim 5, wherein the insert is chosen from a group of inserts, wherein each insert in the group of inserts defines a different insert angle included in the range of 4° to 32°.

7. The system of claim 5, wherein the first and second endplates are fabricated together simultaneously so that the hinge is free to pivot and cannot be disassembled under service conditions.

8. The intervertebral cage of claim 5, wherein the insert is non-adjustable and monolithic.

9. The intervertebral cage of claim 8, wherein the insert forms at least a portion of an anterior end of the intervertebral cage when the insert and the first and second endplates are assembled together.

10. The intervertebral cage of claim 9, wherein the insert forms at least a portion of a superior side of the intervertebral cage when the insert and the first and second endplates are assembled together.

11. A method for implanting an intervertebral cage between adjacent first and second vertebrae to provide a lordotic correction angle between the first and second vertebrae, the method comprising:

providing a first endplate comprising a first vertebra-facing side, an opposite first insert-facing side, and a hinge knuckle that protrudes from the first insert-facing side;

providing a second endplate comprising a second vertebra-facing side, an opposite second insert-facing side, and a receiver formed in the second insert-facing side, wherein the hinge knuckle pivots within the receiver to form a hinge between the first and second endplates;

providing a group of inserts, each insert defining a different insert angle, each insert positionable between the first and second endplates and directly connectable to at least one of the first and second endplates, wherein each insert is non-adjustable and monolithic;

inserting the first and second endplates between the first and second vertebrae;

distracting the first and second vertebrae;

determining in situ the lordotic correction angle between the first and second vertebrae;

selecting an insert from the group of inserts; and positioning the selected insert between the first and second endplates and directly connected to at least one of the first and second endplates to form the lordotic correction angle between the first and second vertebra-facing sides, wherein the intervertebral cage comprises the first endplate, the second endplate, and the selected insert, wherein each insert forms at least a portion of an anterior end of the intervertebral cage and at least a portion of a superior side of the intervertebral cage when that insert and the first and second endplates are assembled together.

12. The method of claim 11, comprising fabricating the first and second endplates together simultaneously so that the hinge is free to pivot and cannot be disassembled under service conditions.

* * * * *